(12) United States Patent
Wijting et al.

(10) Patent No.: US 9,352,151 B2
(45) Date of Patent: *May 31, 2016

(54) METHOD AND APPARATUS FOR APPLYING NEUROMUSCULAR ELECTRICAL STIMULATION

(71) Applicant: Encore Medical Asset Corporation, Henderson, NV (US)

(72) Inventors: Yorick Wijting, Hixson, TN (US); Jeffrey K. Pohl, Soddy Daisy, TN (US)

(73) Assignee: Encore Medical Asset Corporation, Vista, CA (US)

( * ) Notice: Subject to any disclaimer, the term of this patent is extended or adjusted under 35 U.S.C. 154(b) by 138 days.

This patent is subject to a terminal disclaimer.

(21) Appl. No.: 14/144,256

(22) Filed: Dec. 30, 2013

(65) Prior Publication Data

US 2014/0188013 A1    Jul. 3, 2014

Related U.S. Application Data

(63) Continuation of application No. 11/706,455, filed on Feb. 13, 2007, now Pat. No. 8,620,438.

(51) Int. Cl.
*A61N 1/00* (2006.01)
*A61N 1/36* (2006.01)
*A61N 7/00* (2006.01)

(52) U.S. Cl.
CPC .............. *A61N 1/36003* (2013.01); *A61N 7/00* (2013.01)

(58) Field of Classification Search
CPC ..... A61N 1/04; A61N 1/0404; A61N 1/0452; A61N 1/00; A61N 1/0456; A61N 1/36003; A61N 1/36139
See application file for complete search history.

(56) References Cited

U.S. PATENT DOCUMENTS 2,263,205 A    11/1941    Conrad
3,344,792 A    10/1967    Offner et al.
(Continued)

FOREIGN PATENT DOCUMENTS

DE    3216911    11/1983
DE    19545238    5/1997
(Continued)

OTHER PUBLICATIONS

Ilic, Milan et al. "A Programmable Electronic Stimulator for FES Systems" IEEE Transactions on Rehabilitation Engineering, vol. 2, No. 4, Dec. 1994.
(Continued)

*Primary Examiner* — Mallika D Fairchild
(74) *Attorney, Agent, or Firm* — Knobbe Martens Olson & Bear LLP

(57) ABSTRACT

A method and apparatus for applying neuromuscular electrical stimulation to an agonist/antagonist muscle pair to move a limb about a joint includes generating a first pattern of neuromuscular electrical stimulation pulses for output through a first channel to a first pair of electrodes and generating a second pattern of neuromuscular stimulation pulses for output through a second channel to a second pair of electrodes. The first pair of electrodes are attached to the agonist muscle of the agonist/antagonist muscle pair, and the second pair of electrodes are attached to the antagonist muscle. A first pattern of electrical stimulation pulses is transmitted through the first pair of electrodes to the agonist muscle at a first intensity level to initiate contraction of the agonist muscle, and then at a second intensity level which is less than the first intensity level to continue contraction of the agonist muscle. A second pattern of electrical stimulation pulses is transmitted through the second pair of electrodes to the antagonist muscle at a first intensity level to reduce the acceleration of the limb, and then at a second intensity level which is less than the first intensity level to regulate the movement of the limb.

21 Claims, 10 Drawing Sheets

(56) References Cited

U.S. PATENT DOCUMENTS

| | | |
|---|---|---|
| 3,628,538 A | 12/1971 | Vincent et al. |
| 3,810,457 A | 5/1974 | Bottcher et al. |
| 3,895,639 A | 7/1975 | Rodler |
| 3,918,459 A | 11/1975 | Horn |
| 4,019,518 A | 4/1977 | Maurer et al. |
| 4,068,669 A | 1/1978 | Niemi |
| 4,088,141 A | 5/1978 | Niemi |
| 4,164,740 A | 8/1979 | Constant |
| 4,165,750 A | 8/1979 | Aleev et al. |
| 4,177,819 A | 12/1979 | Kofsky et al. |
| 4,256,116 A | 3/1981 | Meretsky et al. |
| 4,324,253 A | 4/1982 | Greene et al. |
| 4,342,317 A | 8/1982 | Axelgaard |
| 4,363,324 A | 12/1982 | Kusserow |
| 4,372,319 A | 2/1983 | Ichinomiya et al. |
| 4,390,023 A | 6/1983 | Rise |
| 4,392,496 A | 7/1983 | Stanton |
| 4,408,609 A | 10/1983 | Axelgaard |
| 4,503,863 A | 3/1985 | Katims |
| 4,535,777 A | 8/1985 | Castel |
| 4,569,352 A | 2/1986 | Petrofsky et al. |
| 4,580,339 A | 4/1986 | Ioffe |
| 4,582,063 A | 4/1986 | Mickiewicz et al. |
| 4,586,495 A | 5/1986 | Petrofsky |
| 4,614,178 A | 9/1986 | Harlt et al. |
| 4,632,117 A | 12/1986 | James |
| 4,640,286 A | 2/1987 | Thomson |
| 4,664,118 A | 5/1987 | Batters |
| 4,669,477 A | 6/1987 | Ober |
| 4,690,145 A | 9/1987 | King-Smith et al. |
| 4,706,674 A | 11/1987 | Dieken et al. |
| 4,769,881 A | 9/1988 | Pedigo et al. |
| 4,785,813 A | 11/1988 | Petrofsky |
| 4,803,988 A | 2/1989 | Thomson |
| 4,805,636 A | 2/1989 | Barry et al. |
| 4,811,742 A | 3/1989 | Hassel et al. |
| 4,848,347 A | 7/1989 | Hall |
| 4,887,603 A | 12/1989 | Morawetz et al. |
| 4,919,139 A | 4/1990 | Brodard |
| 4,926,865 A | 5/1990 | Oman |
| 4,976,264 A | 12/1990 | Petrofsky |
| 4,977,895 A | 12/1990 | Tannenbaum |
| 4,996,987 A | 3/1991 | Petrofsky |
| 5,041,974 A | 8/1991 | Walker et al. |
| 5,048,522 A | 9/1991 | Petrofsky |
| 5,067,478 A | 11/1991 | Berlant |
| 5,067,495 A | 11/1991 | Brehm |
| 5,070,873 A | 12/1991 | Graupe et al. |
| 5,081,989 A | 1/1992 | Graupe et al. |
| 5,092,329 A | 3/1992 | Graupe et al. |
| 5,113,176 A | 5/1992 | Harris |
| 5,117,826 A | 6/1992 | Bartelt et al. |
| 5,123,413 A | 6/1992 | Hasegawa et al. |
| 5,131,401 A | 7/1992 | Westenskow et al. |
| 5,161,530 A | 11/1992 | Gamble |
| 5,178,156 A | 1/1993 | Takishima et al. |
| 5,184,617 A | 2/1993 | Harris et al. |
| 5,233,987 A | 8/1993 | Fabian et al. |
| 5,285,781 A | 2/1994 | Brodard |
| 5,300,096 A | 4/1994 | Hall et al. |
| 5,350,414 A | 9/1994 | Kolen |
| 5,397,338 A | 3/1995 | Grey et al. |
| 5,413,550 A | 5/1995 | Castel |
| 5,507,788 A | 4/1996 | Lieber |
| 5,512,057 A | 4/1996 | Reiss et al. |
| 5,514,165 A | 5/1996 | Malaugh et al. |
| 5,540,235 A | 7/1996 | Wilson |
| 5,540,735 A | 7/1996 | Wingrove |
| 5,562,718 A | 10/1996 | Palermo |
| 5,653,739 A | 8/1997 | Maurer et al. |
| 5,732,401 A | 3/1998 | Conway |
| 5,748,845 A | 5/1998 | Labun et al. |
| 5,755,745 A | 5/1998 | McGraw et al. |
| 5,775,331 A | 7/1998 | Raymond et al. |
| 5,776,171 A | 7/1998 | Peckham et al. |
| 5,776,173 A | 7/1998 | Madsen, Jr. et al. |
| 5,782,893 A | 7/1998 | Dennis, III |
| 5,800,458 A | 9/1998 | Wingrove |
| 5,817,138 A | 10/1998 | Suzuki |
| 5,836,995 A | 11/1998 | MGraw et al. |
| RE35,987 E | 12/1998 | Harris et al. |
| 5,873,900 A | 2/1999 | Maurer et al. |
| 5,954,758 A | 9/1999 | Peckham et al. |
| 5,961,542 A | 10/1999 | Agarwala |
| 5,967,975 A | 10/1999 | Ridgeway |
| 5,980,435 A | 11/1999 | Joutras et al. |
| 6,026,328 A | 2/2000 | Peckham et al. |
| 6,029,090 A | 2/2000 | Herbst |
| 6,041,259 A | 3/2000 | Agarwala et al. |
| 6,044,303 A | 3/2000 | Agarwala et al. |
| RE36,690 E | 5/2000 | McGraw et al. |
| 6,064,911 A | 5/2000 | Wingrove |
| 6,086,525 A | 7/2000 | Davey et al. |
| 6,113,552 A | 9/2000 | Shimazu et al. |
| 6,146,335 A | 11/2000 | Gozani |
| 6,233,472 B1 | 5/2001 | Bennett et al. |
| 6,285,906 B1 | 9/2001 | Ben-Haim et al. |
| 6,292,692 B1 | 9/2001 | Skelton et al. |
| 6,324,432 B1 | 11/2001 | Rigaux et al. |
| 6,393,328 B1 | 5/2002 | McGraw et al. |
| 6,432,074 B1 | 8/2002 | Ager et al. |
| 6,445,955 B1 | 9/2002 | Michelson et al. |
| 6,560,487 B1 | 5/2003 | McGraw et al. |
| 6,564,103 B2 | 5/2003 | Fischer et al. |
| 6,584,358 B2 | 6/2003 | Carter et al. |
| 6,609,031 B1 | 8/2003 | Law et al. |
| 6,612,984 B1 | 9/2003 | Kerr, II |
| 6,628,492 B2 | 9/2003 | Akiyama et al. |
| 6,647,290 B2 | 11/2003 | Wuthrich |
| 6,662,051 B1 | 12/2003 | Eraker et al. |
| 6,675,048 B2 | 1/2004 | McGraw et al. |
| 6,684,106 B2 | 1/2004 | Herbst |
| 6,701,189 B2 | 3/2004 | Fang et al. |
| 6,727,814 B2 | 4/2004 | Saltzstein et al. |
| 6,826,429 B2 | 11/2004 | Johnson et al. |
| 6,839,594 B2 | 1/2005 | Cohen et al. |
| 6,845,271 B2 | 1/2005 | Fang et al. |
| 6,876,883 B2 | 4/2005 | Hurtado |
| 6,907,295 B2 | 6/2005 | Gross et al. |
| 6,963,773 B2 | 11/2005 | Waltman et al. |
| 6,988,005 B2 | 1/2006 | McGraw et al. |
| 2001/0051787 A1 | 12/2001 | Haller et al. |
| 2002/0165590 A1 | 11/2002 | Crowe et al. |
| 2003/0036683 A1 | 2/2003 | Kehr et al. |
| 2003/0065370 A1 | 4/2003 | Lebel et al. |
| 2003/0074037 A1 | 4/2003 | Moore et al. |
| 2003/0120323 A1 | 6/2003 | Meadows et al. |
| 2004/0010291 A1 | 1/2004 | Wagner et al. |
| 2004/0147975 A1 | 7/2004 | Popovic et al. |
| 2004/0167585 A1 | 8/2004 | Kovak et al. |
| 2005/0055054 A1 | 3/2005 | Yu |

FOREIGN PATENT DOCUMENTS

| | | |
|---|---|---|
| DE | 4092175 | 7/1997 |
| EP | 0 269 844 | 6/1988 |
| EP | 0 367 338 | 5/1990 |
| EP | 0 706 806 | 4/1996 |
| EP | 1 095 670 | 5/2001 |
| FR | 2425865 | 12/1979 |
| FR | 2504807 | 11/1982 |
| JP | 2004-0081676 | 3/2004 |
| WO | WO 82/00414 | 2/1982 |
| WO | WO 86/02567 | 5/1986 |
| WO | WO 95/10323 | 4/1995 |
| WO | WO 99/19019 | 4/1999 |
| WO | WO 99/41682 | 8/1999 |
| WO | WO 00/01055 | 1/2000 |
| WO | WO 00/36900 | 6/2000 |
| WO | WO 01/03768 | 1/2001 |
| WO | WO 01/51122 | 7/2001 |
| WO | WO 02/085452 | 10/2002 |
| WO | WO 03/008038 | 1/2003 |
| WO | WO 2004/011087 | 2/2004 |

(56) References Cited

FOREIGN PATENT DOCUMENTS

| WO | WO 2004/012807 | 2/2004 |
|----|----------------|--------|
| WO | WO 2004/018038 | 3/2004 |
| WO | WO 2004/064915 | 8/2004 |

OTHER PUBLICATIONS

Strojnik, P., Peckham, P.H., Chapter 78 Implantable Stimulators for neuromuscular control, The Biomedical engineering handbook, Second Edition, vol. 1, Editor: Joseph D. Bronzino, CRC Press, IEEE Press.

Strojnik, P., Peckham, P.H., Chapter 78 Implantable Stimulators for neuromuscular control, pp. 78-1 to 78-3, the Biomedical engineering handbook, Second Edition, vol. 1, Editor: Joseph D. Bronzino, CRC Press, 1999, Print ISBN: 978-0/8493-8594-0, eBook ISBN: 978-1-4200-4951-0, DOI: 10.1201/9781420049510.ch78.

"Cyclotec Pain Control Products," Cyclotec AMT, 3 pages. Retrieved from http://www.cyclotecamt.com/pages2/products.htm on May 25, 2004.

"Muscle Stimulator and TENS: Very different modalities," RS Medical, 1 page Retrieved from http://www.rsmedical.com/products/diff/body.htm on Apr. 27, 2004.

"Netwave," Blue Sky Labs; 6 pages; Copyright 2003.

"RS-4i Sequential Stimulator," 6 pages; Retrieved from http://www.rsmedical.com/products/rs2/body.htm on Apr. 27, 2004.

"501(k) Summary for netwave Interferential Stimulator," Ryan Telemedicine, LLC; Jun. 12, 2003.

METHOD AND APPARATUS FOR APPLYING NEUROMUSCULAR ELECTRICAL STIMULATION

FIELD OF THE INVENTION

The present invention relates generally to neuromuscular electrical stimulation, and more particularly, to a method and apparatus for applying neuromuscular electrical stimulation for inducing muscle contraction in flexing, extending, adducting or abducting a limb at a joint.

EXPLANATION OF TECHNICAL TERMS

As used herein, the term "burst period" and similar terms refer to the period of time during which the neuromuscular stimulation is applied to the muscles of the patient. As used herein, the term "rest period", "rest interval" and similar terms refer to the period of time between burst periods during which the neuromuscular stimulation is not applied to the muscles of the patient.

As used herein, the terms "frequency", "pulse rate" and similar terms refer to the rate at which neuromuscular electrical stimulation pulses are delivered. The frequency is commonly expressed in hertz (Hz).

As used herein, the terms "pulse width", "pulse duration" and similar terms refer to the duration of the positive phase of the waveform.

BACKGROUND OF THE INVENTION

Neuromuscular electrical stimulation (NMES), sometimes referred to as "functional electrical stimulation" or "FES", is a technique by which muscles are induced to contract by application of electrical stimulation. NMES can be used along with exercise to strengthen an athlete's muscles, or it can be used therapeutically to strengthen and retrain muscles that have been weakened or damaged by disease or traumatic injury. NMES can also be used when voluntary motor ability is irretrievably lost, such as may arise from various forms of paralysis, to induce contractions that provide muscle benefits similar to that obtained by voluntary exercise. NMES may be distinguished from transcutaneous electrical nerve stimulation (TENS) which is used to treat pain by masking pain signals before they reach the brain.

Frequently, NMES has been applied in an attempt to activate muscles over which a patient has little or no conscious control. Thus, for example, U.S. Pat. No. 3,344,792 of Offner et al. describes a method and apparatus for applying NMES to the muscles of the lower leg to aid in walking. According to this patent, one electrode is placed on the skin over the tibialis anticus muscle and another is placed on the skin over the peroneus longus muscle. The two electrodes are then connected to a portable stimulator which is controlled by a pressure-responsive foot switch. The switch is opened when pressure is applied by the heel to the switch, and it is closed when pressure is removed. When the switch is closed, the stimulator unit applies brief pulses of current having a duration of 50 microseconds or less and an amplitude of 50 to several hundred milliamperes. The voltage required is generally on the order of 50-150 volts. As described in the Offner patent, the application of electrical stimulation in this manner not only serves as "a therapeutic method", but also serves as "a substitute for the individual's own nervous system, providing effective utilization of the individual's muscles."

U.S. Pat. No. 4,342,317 of Axelgaard describes a method and apparatus for applying neuromuscular electrical stimulation to the muscles in the thorax for correction of spinal curvature deficiencies. According to this patent, a pair of specific muscle sites within the muscle group to be treated are selected, so that stimulation of the two muscle sites, on an alternating basis, will not result in any overlap of stimulation. A dual channel alternating stimulator is employed to generate alternating ON/OFF waveforms for each channel. The amplitude of the stimulating pulses is within the range of 60-80 milliamperes, and the ON/OFF times for each of the two channels are adjusted so that one muscle group starts to contract while the other starts to relax, and vice-versa.

U.S. Pat. No. 4,392,496 of Stanton describes a dual-channel neuromuscular electrical stimulator which is adapted for neuromuscular stimulation at two sites for exercising muscles to prevent disuse atrophy while minimizing fatigue. The stimulator provides, on two output channels, alternating pulsed stimulation signals which are increased in intensity at a variable rate until a fixed intensity is reached. The pulses are applied during an adjustable predetermined stimulation period and removed during an adjustable predetermined resting interval. In the preferred embodiment of the invention, the pulse rate is adjustable between 3 and 50 pulses per second.

U.S. Pat. No. 4,569,352 of Petrofsky et al. describes a feedback control system that employs a plurality of sensors and electrodes through which neuromuscular electrical stimulation is applied to enable standing and walking by paraplegic and quadriplegic persons. A programmed microprocessor produces hip movement by generating control signals for stimulation transducers which stimulate the iliacus and hamstring muscles. Knee flexion is produced by transducers which stimulate the quadriceps muscles, and ankle movement is produced by stimulating the gastrocnemius and tibialis muscles. The stimulation circuitry creates a series of alternating pulses at a frequency of 50 Hz.

U.S. Pat. No. 4,586,495 of Petrofsky describes a method and apparatus for stimulating the muscles of a patient who has suffered a spinal cord injury during the period following the injury and prior to the time when stimulated dynamic exercise may be commenced according to the method and apparatus of U.S. Pat. No. 4,569,352. The apparatus of the '495 patent includes a leg brace which maintains the knee and ankle at predetermined angles. Electrodes are applied to the muscles of the braced leg over the agonist and antagonist muscles for bending the leg about the knee and ankle joints. The hamstring and quadriceps muscles function as agonist and antagonist muscles, respectively, for the knee joint and the tibialis anterior and gastrocnemius muscles function as agonist and antagonist muscles, respectively, for the ankle joint. In the preferred embodiment of the invention, the quadriceps muscles are stimulated for approximately four seconds to cause the muscles to attempt extension against the restraint of the brace. Thereafter, the quadriceps muscles are rested and the hamstring muscles are stimulated for four seconds to cause the muscles to attempt to bend the knee against the restraint of the brace. Then both sets of muscles are rested for four seconds, and the sequence is repeated. After the hamstring and quadriceps muscles have been exercised, the electrodes are placed on the tibialis anterior and gastrocnemius muscles and a similar stimulation sequence is begun for these muscles. A pair of load cells on the leg brace provide feedback signals to a computer which controls the application of the electrical stimulation signals. As the muscles tire with exertion, the computer increases the stimulation level until a maximum value of 50 volts is reached. Each stimulation signal comprises a series of pulses having a pulse width of about 300 microseconds and a frequency of 40 pulses/second.

As mentioned above, NMES can be used along with exercise to strengthen an athlete's muscles, or it can be used therapeutically to strengthen and retrain muscles that have been weakened or damaged by disease or traumatic injury. Thus, for example, U.S. Pat. No. 4,622,973 of Agarwala describes a clinical device which may be used to establish an NMES regimen, as well as a portable device which is programmable by the clinical device and which automatically reproduces the NMES regimen which was established in the clinical device.

U.S. Pat. No. 4,996,987 of Petrofsky describes a method and apparatus for applying electrical stimulation to induce work-producing contraction of the muscles. According to this patent, the stimulation of work-producing contraction of muscles in patients with little or no nerve damage causes unacceptable pain. Consequently, the method of the invention includes applying a high-frequency, low-amplitude desensitizing current to the muscle to be stimulated prior to applying a low-frequency, high-amplitude stimulating current which is continuous with the desensitizing current. The stimulating current is applied as the desensitizing current is terminated, and the two currents are alternately applied so that no abrupt discontinuity occurs between the currents. Preferably, the stimulating current is a "camel-back" biphasic signal having three segments, the first and third of which are of opposite polarity to the second. The first and third segments are substantially identical in duration and magnitude, and the second has a duration equal to the sum of the durations of the first and third segments and a magnitude that is equal to and of opposite polarity to either the first or the third segment.

U.S. Pat. No. 5,562,718 of Palermo describes a device for use in applying NMES in a series of electrical pulses in the form of sequential pulse patterns, or dual or triple overlapping pulse patterns. These electrical pulse patterns are applied through a first channel by electrodes that are attached to the skin over an agonist muscle and through a second channel by electrodes that are attached to the skin over the corresponding antagonist muscle. The timing of the sequential or overlapping pulse train patterns is reportedly selected to take advantage of central nervous system inhibition and facilitation by repetitive cycling of the pulse trains to emulate reciprocating limb speeds ranging from slow gentle arm or leg movements to the fastest running patterns. The commercial embodiment of the Palermo device, marketed by Accelerated Care Plus of Reno, Nev., employs electrodes applied to the agonist and antagonist muscles to generate overlapping pulse patterns that serve to contract these muscles. According to literature published by Accelerated Care Plus, a first pulse pattern is applied through a first channel to the agonist muscle in a first burst period of approximately 75 msec., followed by a first rest interval of about 50 msec. and a second pulse pattern in a second burst period of about 50 msec. A third pulse pattern is then delivered to the antagonist muscle through the second channel in a third burst period of about 75 msec., which begins approximately 55 msec. after the beginning of the first burst period (of the first channel) and continues through the first rest interval (of the first channel) and for about 10 msec. into the second burst period.

U.S. Pat. No. 5,980,435 of Joutras et al. describes a method and apparatus for therapeutic use of a jointed brace. According to this patent, the brace is attached to a jointed limb and provides controlled resistance to movement of the limb about the joint. The brace may used in conjunction with a neuromuscular stimulation device, and it may be programmed to resist the movement of stronger, or antagonistic, muscles against weaker, or agonistic, muscles. However, there is no force applied by the equipment to the user in the absence of an attempt to move a limb about a joint. The force applied by the equipment is only a force of reaction.

U.S. Pat. No. 6,845,271 of Fang et al. describes a method and apparatus for treatment of shoulder dysfunction using neuromuscular electrical stimulation applied through intramuscular electrodes. Preferably, the method involves asynchronous stimulation of more than one muscle group, such as a first muscle group being the supraspinatus in combination with the middle deltoid and a second muscle group being the trapezious in combination with the posterior deltoid. This asynchronous stimulation involves intermittent periods of stimulation and rest, with one muscle group being subjected to stimulation while the other is resting.

Although it is known to apply NMES to the agonist and corresponding antagonist muscles in certain pulse patterns, the inventors have developed a method and apparatus for generating NMES pulses in patterns that appear to more accurately simulate natural movement of a limb about a joint.

SUMMARY OF THE INVENTION

The invention comprises a method and apparatus for applying neuromuscular electrical stimulation to an agonist/antagonist muscle pair to move a limb about a joint. According to this method, a device is provided for generating a first pattern of neuromuscular electrical stimulation pulses for output through a first channel to a first pair of electrodes and for generating a second pattern of neuromuscular stimulation pulses for output through a second channel to a second pair of electrodes. A first pair of electrodes is provided in operative connection to the first channel of the device, and a second pair of electrodes is provided in operative connection to the second channel of the device. The first pair of electrodes is attached to the agonist muscle of the agonist/antagonist muscle pair, and the second pair of electrodes is attached to the antagonist muscle of the muscle pair. A first pattern of electrical stimulation pulses is generated for transmission through the first pair of electrodes to the agonist muscle at a first intensity level for a period sufficient to initiate contraction of the agonist muscle, and then at a second intensity level which is less than the first intensity level for a period sufficient to continue contraction of the agonist muscle. A second pattern of electrical stimulation pulses is generated for transmission through the second pair of electrodes to the antagonist muscle at a first intensity level for a period sufficient to reduce the acceleration of the limb, and then at a second intensity level which is less than the first intensity level for a period sufficient to regulate the movement of the limb.

In order to facilitate an understanding of the invention, the preferred embodiments of the invention are illustrated in the drawings, and a detailed description thereof follows. It is not intended, however, that the invention be limited to the particular embodiments described or to use in connection with the apparatus illustrated herein. Various modifications and alternative embodiments such as would ordinarily occur to one skilled in the art to which the invention relates are also contemplated and included within the scope of the invention described and claimed herein.

BRIEF DESCRIPTION OF THE DRAWINGS

The presently preferred embodiments of the invention are illustrated in the accompanying drawings, in which like reference numerals represent like parts throughout, and in which.

DESCRIPTION OF THE PREFERRED EMBODIMENTS OF THE INVENTION

Figure 1:
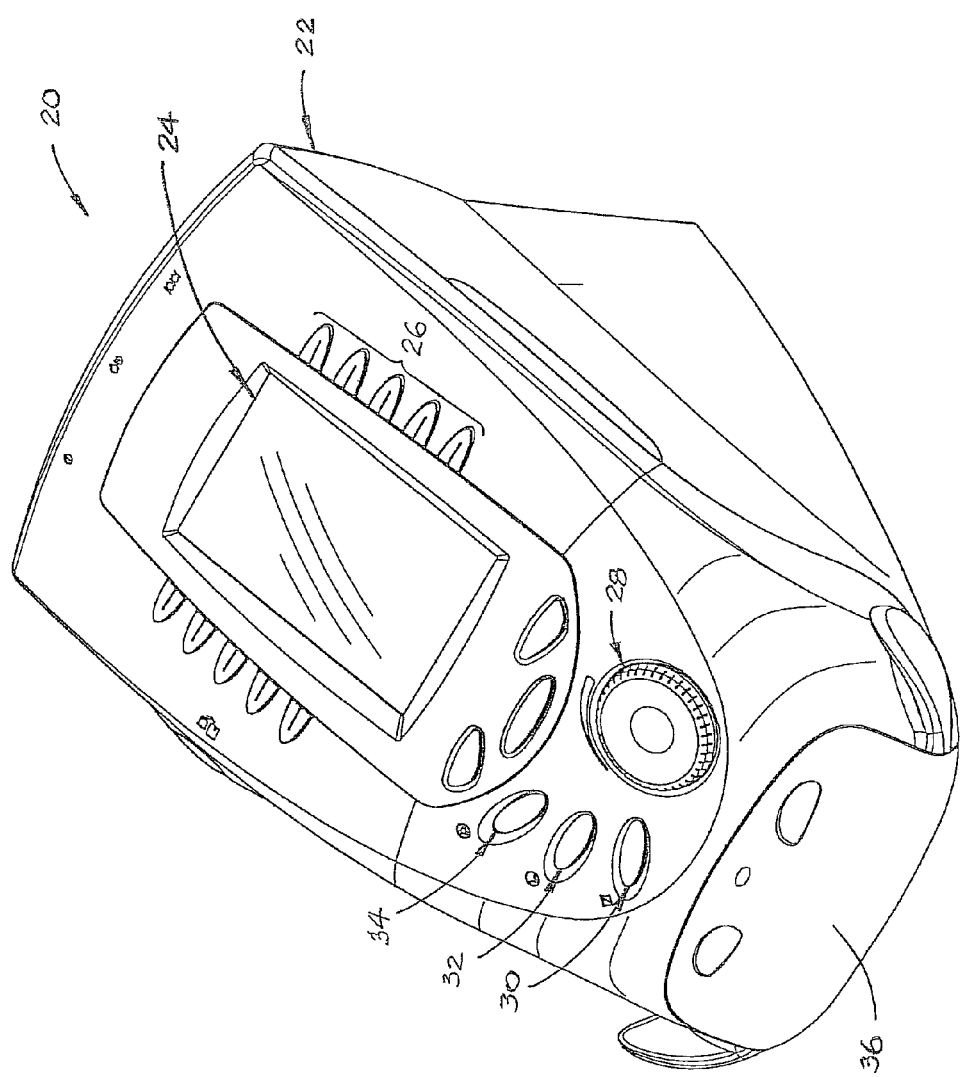
FIG. 1 is a first embodiment of a device that may be used in applying neuromuscular electrical stimulation to an agonist/antagonist muscle pair to move a limb about a joint.
Figure 2:
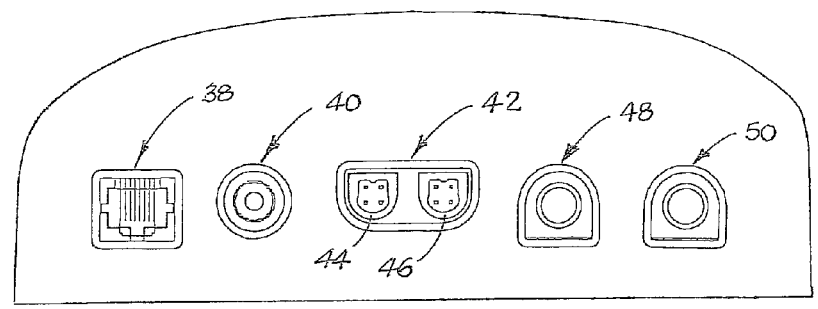
FIG. 2 is a front view of a portion of the device of FIG. 1, with the front access panel removed.

FIGS. 1-4 illustrate a preferred embodiment of a device for generating neuromuscular electrical stimulation for inducing muscle contraction in flexing or abducting a limb at a joint. As shown therein, device 20 comprises the main component of a modular system for providing the therapeutic application of energy in multiple forms. Device 20 comprises a combination two-channel electrotherapy and ultrasound system, which includes cabinet 22 having display screen 24. Device 20 also includes a user interface in the form of function keys 26 (including keys on both sides of the display screen), which form a part of the interactive interface of the device. Other function keys include knob 28 which provides therapy "Intensity Control" and button 30, which is a therapy session "Start" key. Button 32 is a therapy session "Pause" key and button 34 is a therapy session "Stop" key. Front access panel 36 provides access to a plurality of outlet jacks (shown in FIG. 2), including operator remote control connector 38, patient interrupt switch connector 40, electrical stimulation outlet jack 42 (comprised of channel 1 connector 44 and channel 2 connector 46), microcurrent probe connector 48 (for use when electrical stimulation is applied using a microcurrent waveform) and ultrasound applicator connector 50. The generators for the patterns of electrical stimulation pulses that are applied according to the invention are located in device 20.

Figure 3:
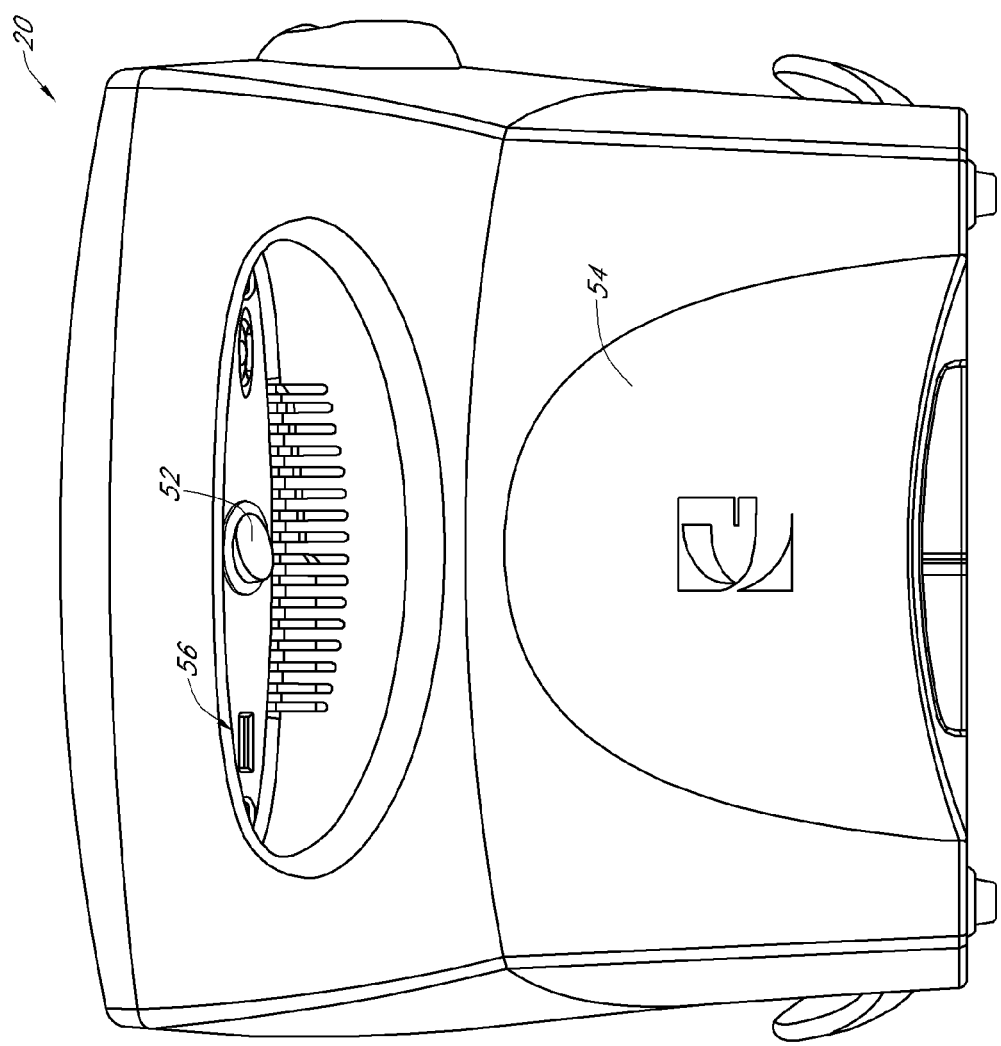
FIG. 3 is a rear view of the device of FIG. 1.
Figure 4:
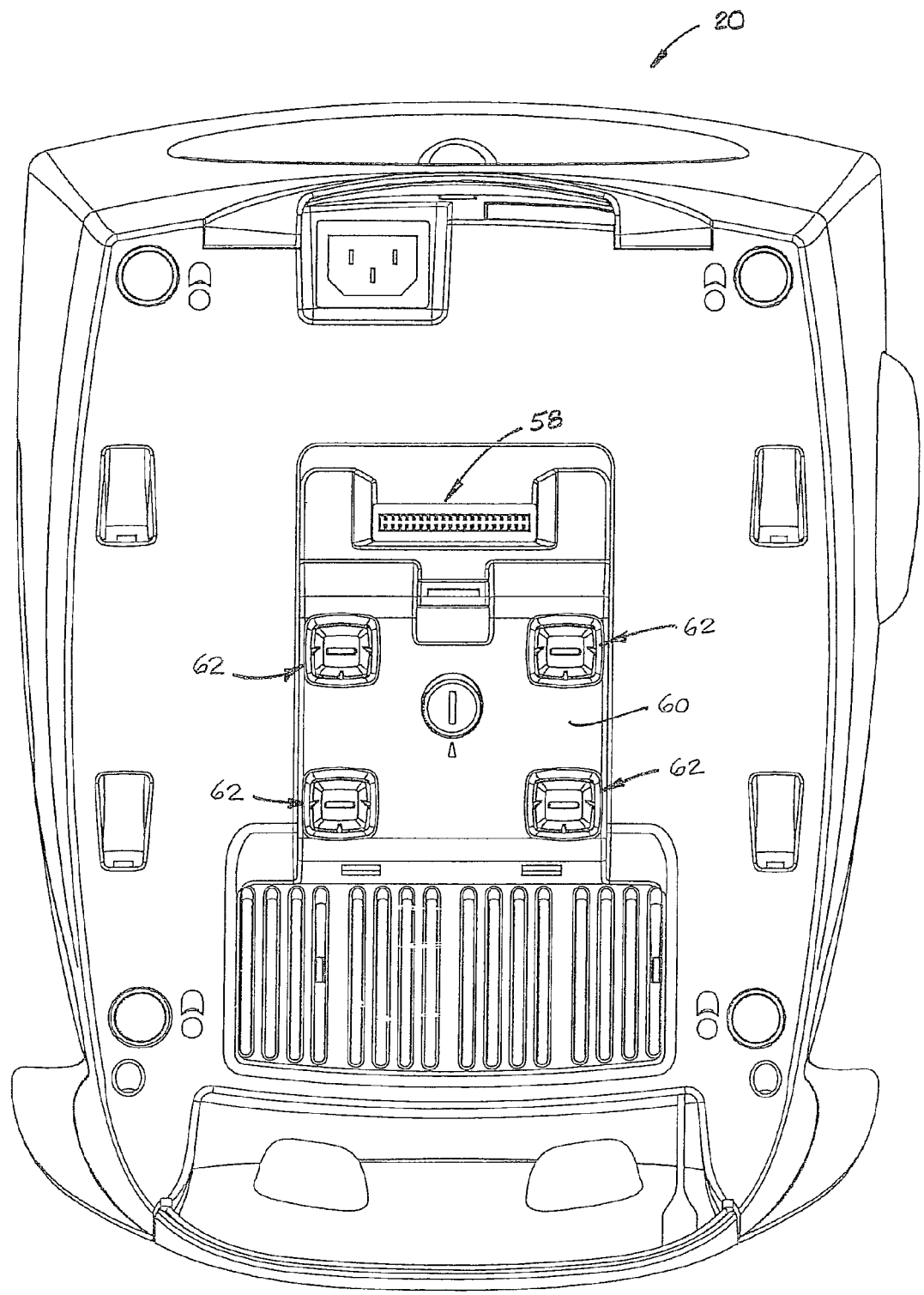
FIG. 4 is a bottom view of the device of FIG. 1.

FIG. 3 shows the rear of device 20 illustrating system power switch 52 and rear access panel 54, behind which is located the main power cord (not shown). FIG. 3 also shows the location of serial connector outlet jack 56 for connection of a serial device (not shown) such as a hand dynamometry device, an electrogoniometry device or a pressure pad transducer. FIG. 4 shows the bottom of device 20, including a first module receiver which is adapted to receive several types of upgrade modules for enhancing the operation of the system. This first module receiver comprises ribbon cable connector 58 to which an associated ribbon cable (not shown) may be attached. The first module receiver is adapted to receive an upgrade module such as a rechargeable battery module, a vacuum electrode module (which is adapted to permit the application of electrical stimulation using vacuum electrodes instead of adhesively applied electrodes), a module that is adapted to generate energy in the form of electromagnetic radiation (such as an LLLT module) or other types of upgrade modules. Referring again to FIG. 4, a second module receiver 60, which includes PC board contacts 62, is adapted to receive another type of upgrade module for enhancing the operation of device 20, such as an EMG module (not shown).

Figure 6:
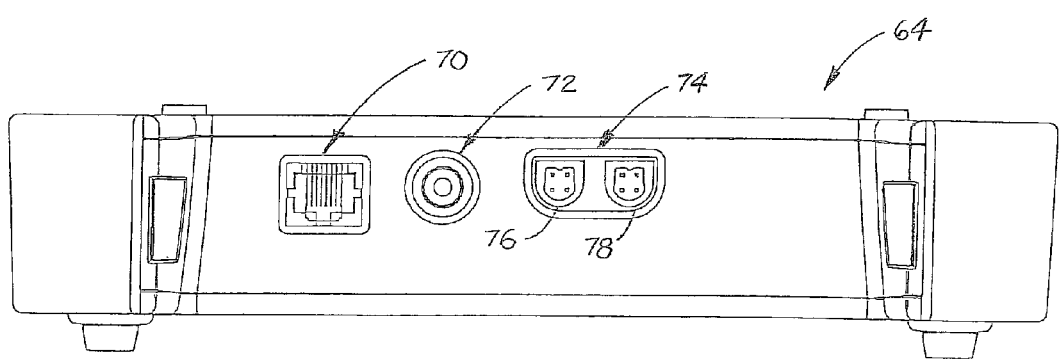
FIG. 6 is a front view of a module which comprises a portion of the apparatus of FIG. 5.
Figure 5:
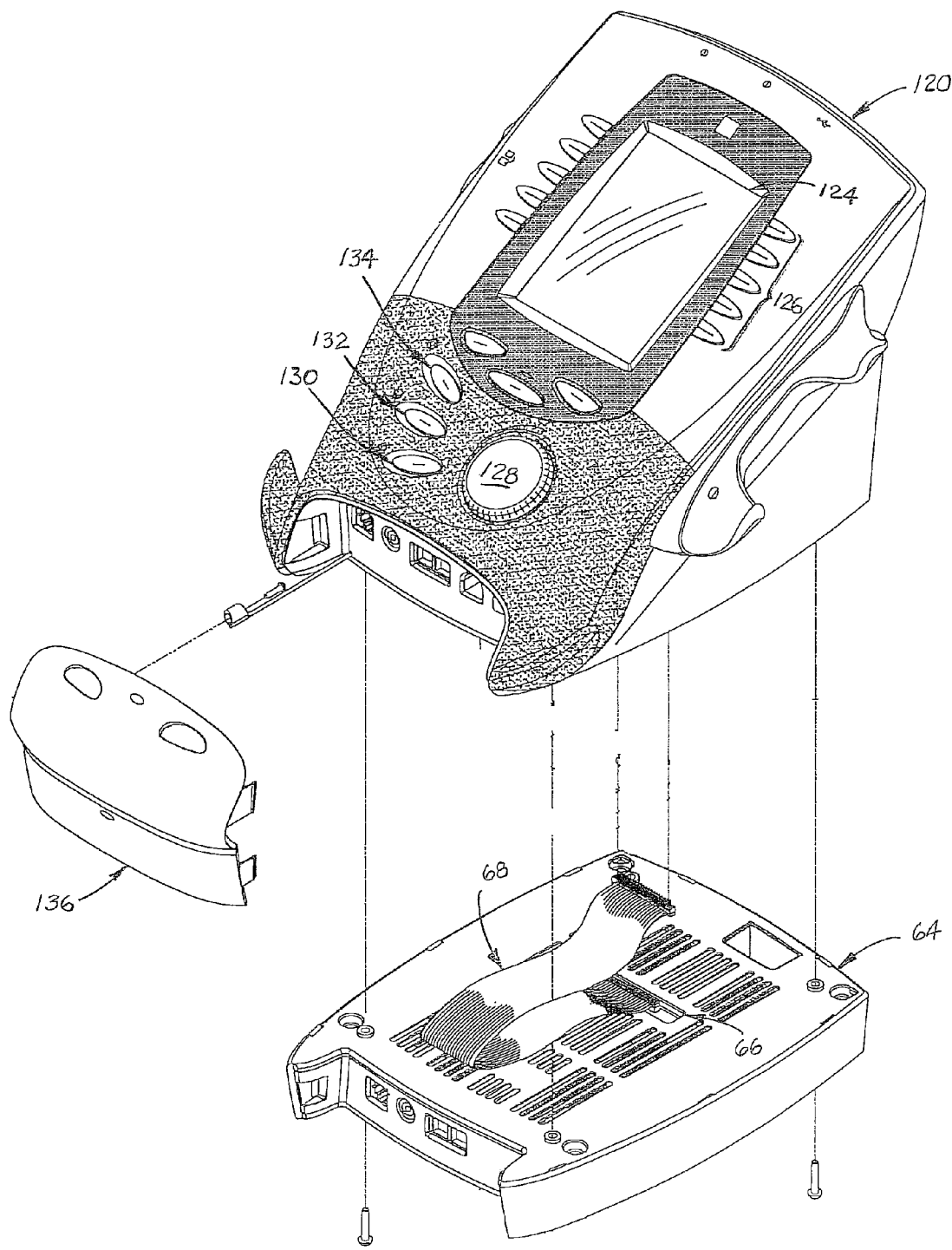
FIG. 5 is an exploded perspective view of a second embodiment of an apparatus that may be used in applying neuromuscular electrical stimulation to an agonist/antagonist muscle pair to move a limb about a joint.
Figure 7:
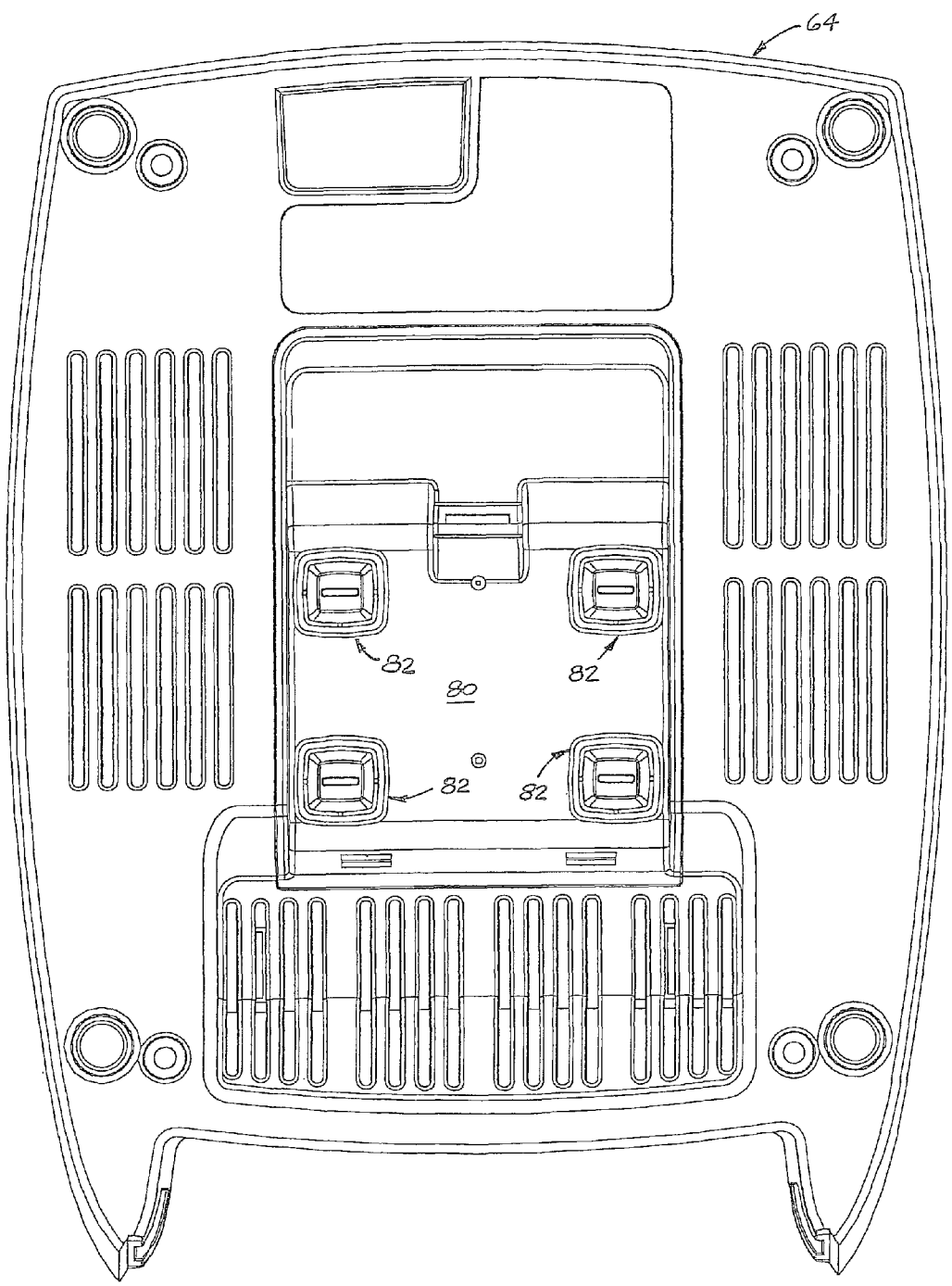
FIG. 7 is a bottom view of the module illustrated in FIGS. 5 and 6.

FIG. 5 illustrates an alternative embodiment of an apparatus for providing neuromuscular electrical stimulation according to the invention. As shown therein, device 120 is adapted to provide electrotherapy and/or ultrasound therapy, but does not provide the patterns of electrical stimulation pulses that are applied according to the invention without upgrade module 64. Device 120 includes cabinet 122 having display screen 124 and a user interface in the form of function keys 126 (including keys on both sides of the display screen), which form a part of the interactive interface of the device. Other function keys include knob 128 which provides therapy "Intensity Control" and button 130, which is a therapy session "Start" key. Button 132 is a therapy session "Pause" key and button 134 is a therapy session "Stop" key. Attached to device 120 is two-channel electrical stimulation upgrade module 64 for generating the electrical stimulation pulses that are applied through channels 1 and 2 according to the invention. Module 64 (also shown in FIGS. 6 and 7) includes ribbon cable connector 66 to which is attached one end of ribbon cable 68. The other end of ribbon cable 68 is attached to a first module receiver of device 120 (comprising a ribbon cable connector, not shown, but similar to ribbon cable connector 58 of device 20). Device 120 also includes front access panel 136 which is similar to, but larger than, front access panel 36 of device 20. As shown in FIG. 6, module 64 includes a plurality of outlet jacks, such as operator remote control connector 70, patient interrupt switch connector 72 and electrical stimulation outlet jack 74 (comprised of channel 1 connector 76 and channel 2 connector 78). FIG. 7 illustrates a bottom view of module 64. As shown therein, it is preferred that module 64 include secondary module receiver 80 which is essentially identical to second module receiver 60 of device 20. Secondary module receiver 80, which includes PC board contacts 82, is adapted to receive another type of upgrade module for enhancing the operation of the system, such as an EMG module.

Figure 8:
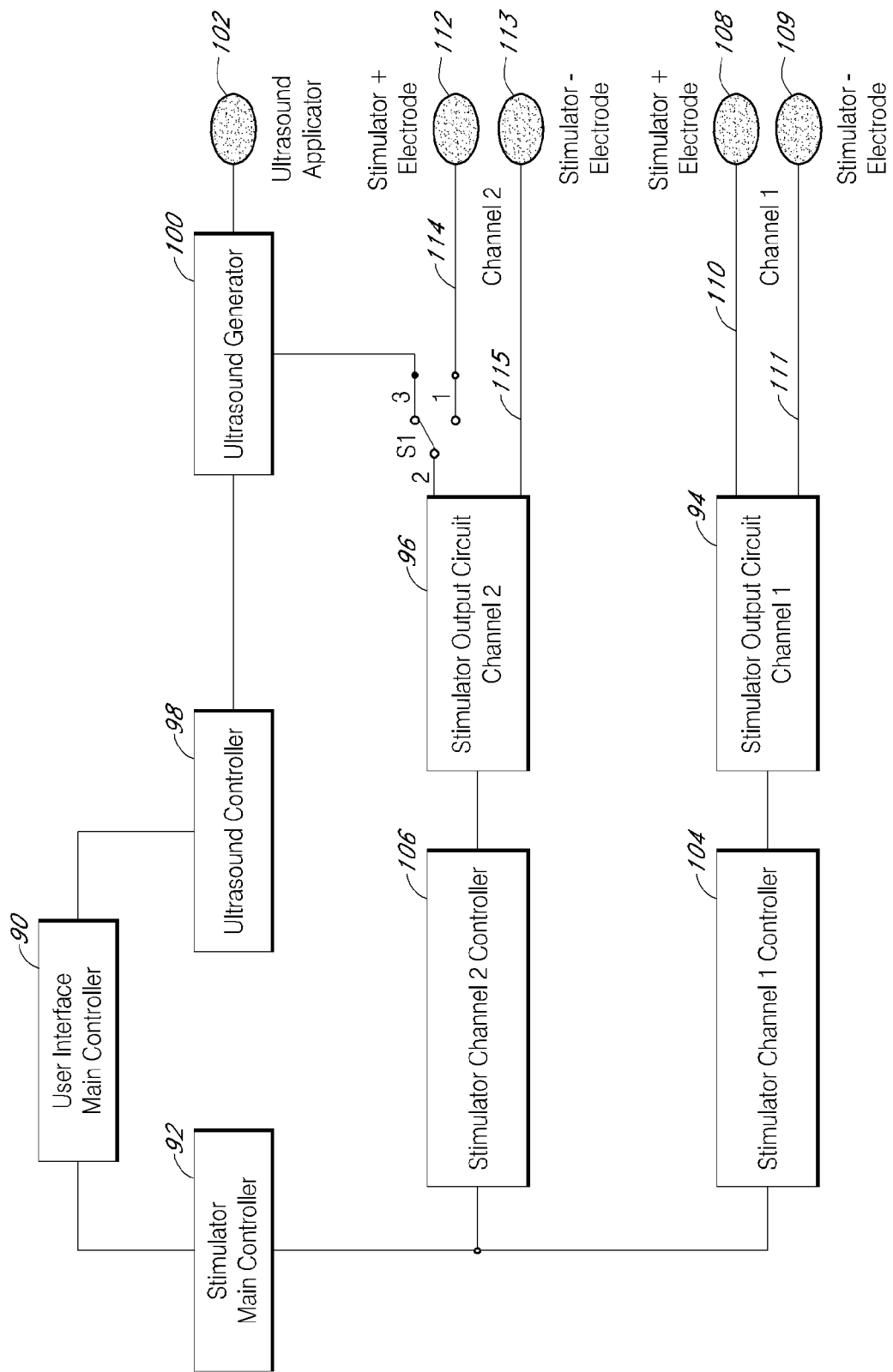
FIG. 8 is a block diagram illustrating the operation of the device of FIGS. 1-4 or the apparatus of FIGS. 5-7.

Referring now to FIG. 8, the operation of the embodiment of FIGS. 1-4 or the embodiment of FIGS. 5-7 is illustrated. As shown therein, interface/main controller 90 is the control interface for the user and the primary controller for device 20 (or device 120 and attached module 64). Major components include a graphic display (such as display screen 24 of device 20 or display screen 124 of device 120), display controller, power supply controls, pushbuttons (including function keys 26 of device 20 or function keys 126 of device 120), and a power switch (such as power switch 52 of device 20). As described above, this interface allows the user to select the treatment parameters desired and to control the application of neuromuscular electrical stimulation during treatment.

Stimulation main controller 92 comprises the communication interface between stimulation channel 1 controller 104, stimulation channel 2 controller 106 and user interface/main controller 90. Stimulation controller 92 gets the treatment parameters from the user interface controller 90 and passes them on to the stimulator channels. Stimulation main controller 92 also passes operational parameters from stimulator channel 1 controller 104 and stimulation channel 2 controller 106 back to user interface/main controller 90.

Ultrasound controller 98 provides the communication interface between ultrasound generator 100 and user interface/main controller 90. Ultrasound controller 98 gets the treatment parameters from user interface controller 90 and sets up ultrasound generator 100 for proper output through ultrasound applicator 102. The ultrasound controller also passes operational parameters from ultrasound generator 100 back to user interface/main controller 90. Preferably, ultrasound generator 100 produces electrical energy at a frequency of approximately 1 MHz or 3.3 MHz. When connected to the ultrasound applicator it generates ultrasound at these frequencies. Stimulation from channel 2 output circuit can be routed through the ultrasound generator and out to the ultrasound applicator when so desired. This is accomplished with relay switch S1 and is engaged as shown in FIG. 8 (so that contact 2 is in electrical communication with contact 3), when the user desires apply therapeutic treatment with both electrical stimulation and ultrasound simultaneously.

Stimulator channel 1 controller 104 controls stimulator channel 1 output circuitry 94 which generates the user selected waveform, including the electrical stimulation pulses that are applied through channel 1 according to the invention. Controller 104 controls and monitors both voltage and current passing to the patient through channel 1, and it provides feedback status information to stimulator main controller 92. Stimulator output circuit 94 for channel 1 is a variable high voltage power supply capable of generating voltages of up to 500 volts and continuous currents as high as 250 mA. The patient is connected to the output circuitry through switching devices that deliver stimulation based on the user selected waveform. The output can be controlled by maintaining either constant current or constant voltage. The output can also be dynamically controlled over time, varying in both amplitude and frequency.

Stimulator channel 2 controller 106 controls stimulator channel 2 output circuitry 96 which generates the user selected waveform, including the electrical stimulation pulses that are applied through channel 2 according to the invention. Controller 106 controls and monitors both voltage and current passing to the patient through channel 2. Controller 106 also provides feedback status information to stimulator main controller 92. Stimulator output circuit 96 for channel 2 is a variable high voltage power supply capable of generating voltages of up to 500 volts and continuous currents as high as 250 mA. The patient is connected to the output circuitry through switching devices that deliver stimulation based on the user selected waveform. Like the output from channel 1, the output from channel 2 can be controlled by maintaining either constant current or constant voltage. The output can also be dynamically controlled over time, varying in both amplitude and frequency. The positive (+) output connection from channel 2 can be routed through ultrasound generator 100 to the ultrasound applicator when this mode of operation is selected by use of switch S1 so that contact 2 is in electrical communication with contact 1 (not shown).

Figure 9:
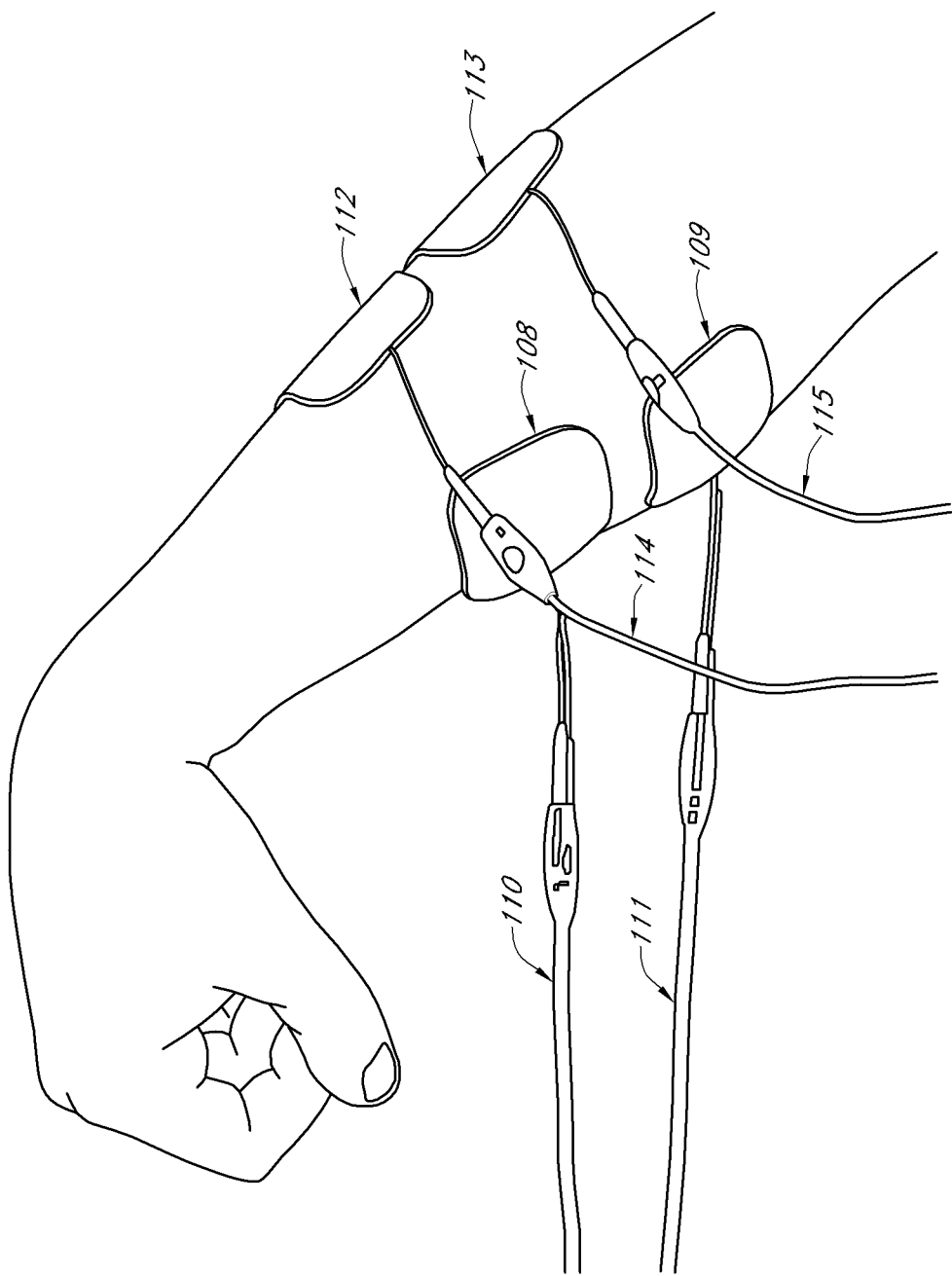
FIG. 9 is a perspective view of a patient's arm showing two pairs of electrodes which may be employed in the practice of a preferred embodiment of the invention.

The invention comprises a method and apparatus for applying neuromuscular electrical stimulation to an agonist/antagonist muscle pair to move a limb about a joint. Such agonist/antagonist muscle pairs may include (among others) the biceps and triceps for moving the forearm about the elbow joint, finger flexors and finger extensors for moving the fingers about various finger joints, the wrist flexors and wrist extensors for moving the hand about the wrist joint, the quadricep and hamstring for moving the lower leg about the knee joint and the anterior tibialis and gastroc/soleus for moving the foot about the ankle joint. According to the method of the invention, a device, such as device 20 or the device 120/module 64 combination, is provided for generating a first pattern of neuromuscular electrical stimulation pulses for output through a first channel to a first pair of electrodes and a second pattern of neuromuscular stimulation pulses for output through a second channel to a second pair of electrodes. FIG. 9 illustrates the application of electrode 108 and electrode 109 from channel 1 to the skin over the wrist and finger flexor muscles (the agonist) of the forearm, although the relative positions of the electrodes of channel 1 may be reversed, or the electrodes may be placed in different positions. Electrode 108 is operatively attached to channel 1 output circuit 94 (shown in FIG. 8) by electrode lead 110, and electrode 109 is operatively attached to channel 1 output circuit 94 by electrode lead 111. Similarly, electrode 112 and electrode 113 from channel 2 are applied to the skin over the wrist and finger extensor muscles (the antagonist) of the forearm, although the relative positions of the electrodes of channel 2 may be reversed, or the electrodes may be placed in different positions. Electrode 112 is operatively attached to channel 2 output circuit 96 (shown in FIG. 8) by electrode lead 114, and electrode 113 is operatively attached to channel 2 output circuit 96 by electrode lead 115. The electrodes from each channel are preferably placed no further apart than the length (or diameter) of the smallest electrode. Preferably, the electrode pairs should be positioned longitudinally with respect to the direction of the muscle fibers. The electrodes of channel 1 are preferably placed on either end of the muscle bellies of the agonist muscle (or muscle group) and the electrodes of channel 2 are preferably placed on either end of the muscle bellies of the corresponding antagonist muscle (or muscle group).

Figure 10:
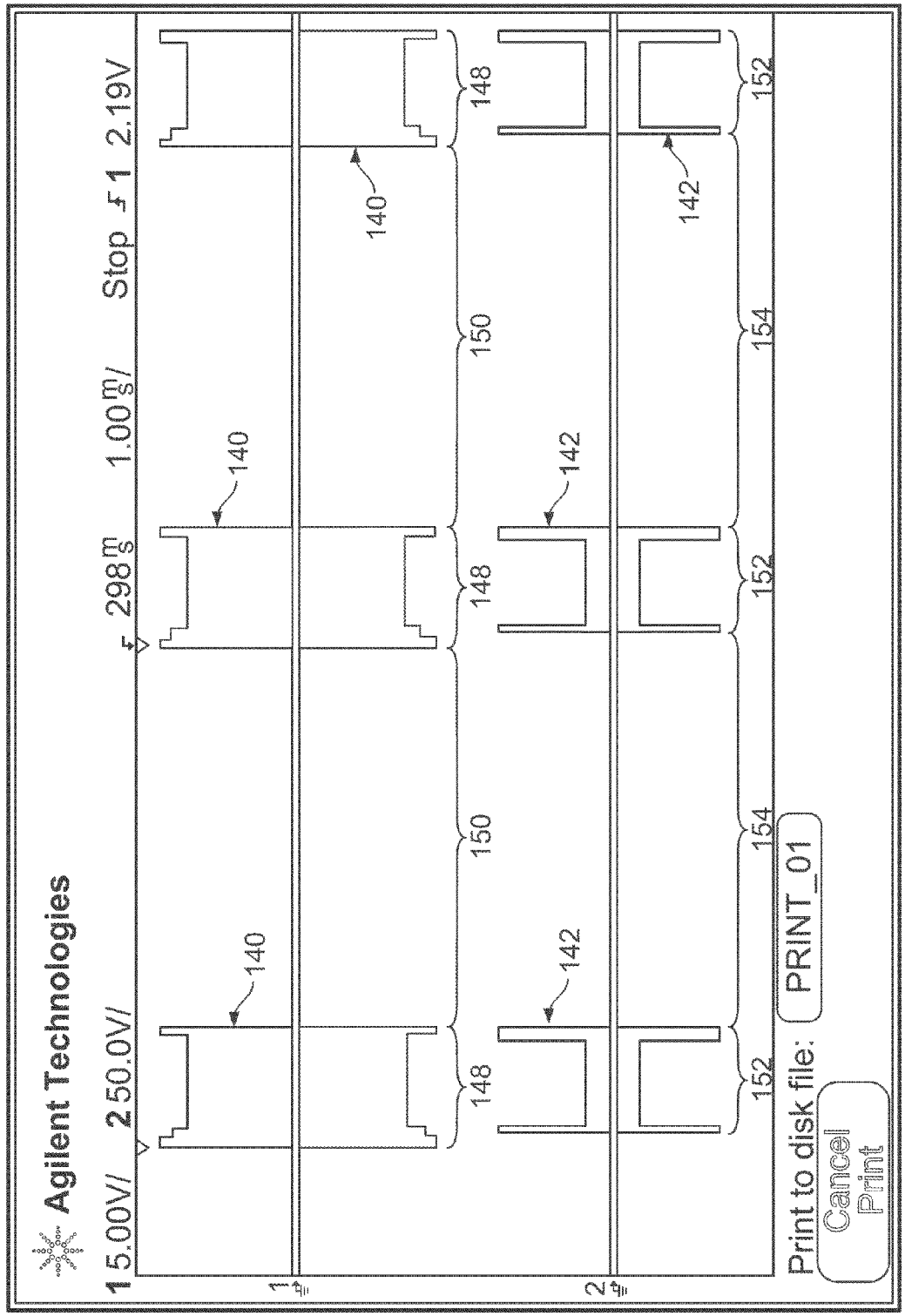
FIG. 10 is a graphical illustration of patterns of electrical stimulation pulses which may be transmitted to an agonist muscle and corresponding patterns of electrical stimulation pulses which may be transmitted to the associated antagonist muscle according to a preferred embodiment of the invention. The X-axis shows elapsed time and the Y-axis shows the intensity of the electrical stimulation pulses.

When the first pair of electrodes 108 and 109 are properly attached to make electrical contact with the agonist muscles of the patient and to conduct neuromuscular electrical stimulation pulses from channel 1 output circuit 94 of device 20 (or the combination of device 120 and module 64), and the second pair of electrodes 112 and 113 are properly attached to make electrical contact with the antagonist muscles of the patient and to conduct neuromuscular electrical stimulation pulses from channel 2 output circuit 96, a first pattern 140 of electrical stimulation pulses (shown in FIGS. 10 and 11) are generated for transmission through the first pair of electrodes to the agonist muscle, and a second pattern 142 of electrical stimulation pulses are generated for transmission through the second pair of electrodes to the antagonist muscle. Preferably, the first pattern of electrical stimulation comprises a series of pulses, each of which has a pulse duration within the range of 20-400 μsec., most preferably within the range of 100-400 μec. It is also preferred that the second pattern of electrical stimulation comprises a series of pulses, each of which has a pulse duration within the range of 20-400 μsec., and most preferably within the range of 100-400 μsec. Further, it is preferred that the first pattern 140 of electrical stimulation pulses be generated during a plurality of first burst periods 148, each of which has a duration within the range of 200-5000 msec., and that each first burst period be followed by a rest period or rest interval during which no electrical stimulation pulses are generated for transmission through the first channel. Preferably, each first burst period 148 is followed by a rest period 150 which has a duration at least 2-5 times the duration of the preceding first burst period. Similarly, it is preferred that the second pattern 142 of electrical stimulation pulses be generated during a plurality of second burst periods 152, each of which begins after the beginning of a first burst period and ends no later than (and most preferably simultaneously with) the end of the first burst period. It is also preferred that each of second burst periods 152 has a duration within the range of 200-5000 msec., and that each second burst period is followed by a rest period or rest interval during which no electrical stimulation pulses are generated for transmission through the second channel. Preferably, each second burst period 152 is followed by a rest period 154 which has a duration at least 2-5 times the duration of the preceding second burst period.

It is also preferred that the first pattern of electrical stimulation pulses be generated or provided in a waveform selected from the group consisting of symmetrical biphasic, asymmetrical biphasic, high volt and premodulated (most preferably symmetrical biphasic), and that the second pattern of electrical stimulation pulses be generated or provided in a waveform selected from the group consisting of symmetrical biphasic, asymmetrical biphasic, high volt and premodulated (most preferably symmetrical biphasic). Furthermore, it is preferred that first pulse pattern generating circuit 94 be adapted to generate a first pattern of electrical stimulation pulses having a frequency 144 within the range of 20-80 Hz and an intensity (or intensities) within the range of 10-150 mA., and that second pulse pattern generating circuit 96 be adapted to generate a second pattern of electrical stimulation pulses having a frequency 146 within the range of 20-80 Hz and an intensity (or intensities) within the range of 10-150 mA.

Figure 11:
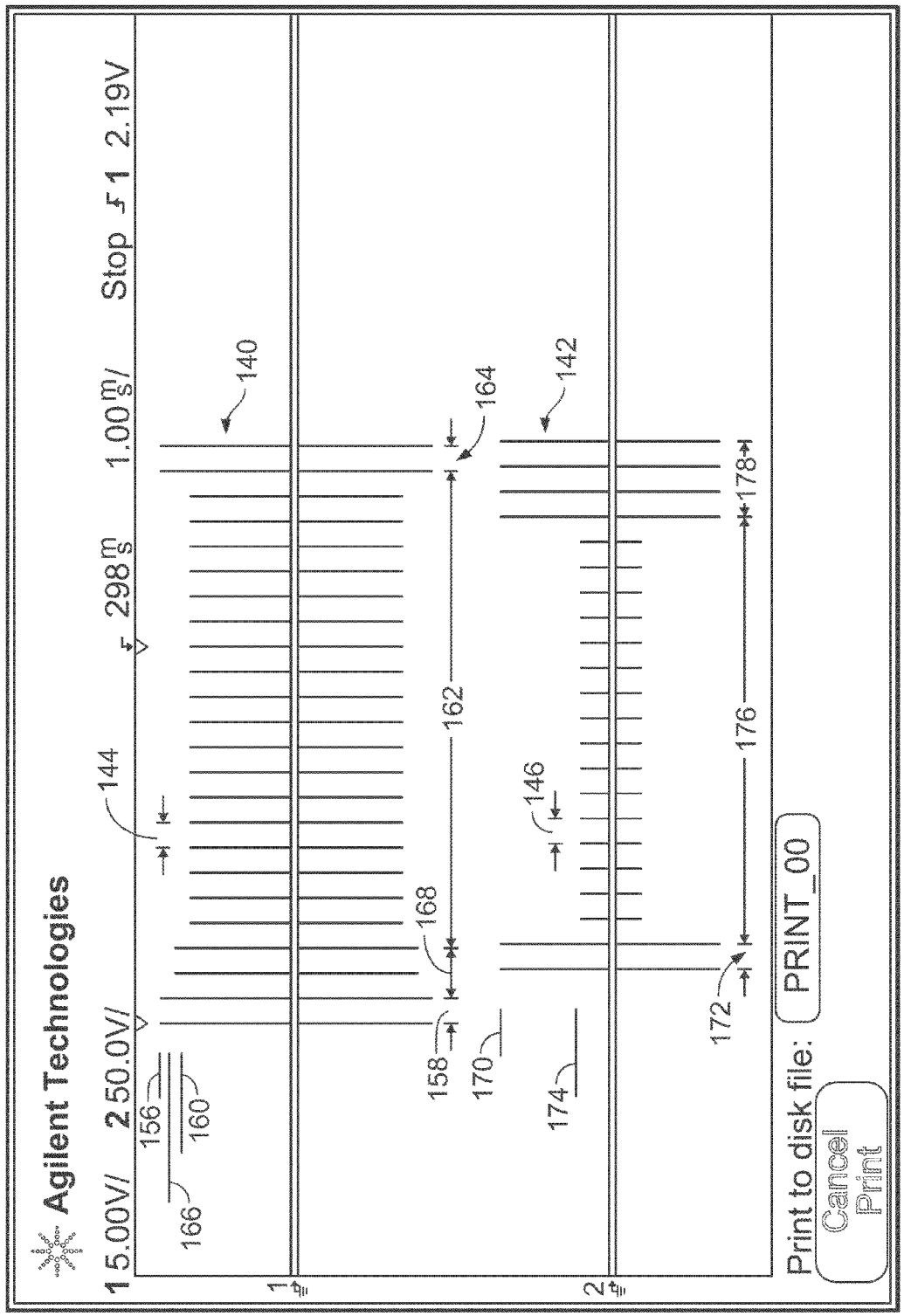
FIG. 11 is a detailed illustration of one of the patterns of electrical stimulation pulses which may be transmitted to an agonist muscle and the corresponding pattern of electrical stimulation pulses which may be transmitted to the associated antagonist muscle according to a preferred embodiment of the invention. The X-axis shows elapsed time and the Y-axis shows the intensity of the electrical stimulation pulses.

As shown in FIG. 11, preferred first pulse pattern generating circuit 94 is adapted to generate a first pattern of electrical stimulation pulses for transmission through a first pair of electrodes 108 and 109 to the agonist muscle at a first intensity level 156 for a period 158 which is sufficient to initiate contraction of the agonist muscle, and at a second intensity level 160 which is less than the first intensity level (and most preferably 75-90% of the first intensity level) for a period 162 that is sufficient to continue contraction of the agonist muscle, and at a third intensity level which is greater than the second intensity level (and most preferably equal to the first intensity level 156) for a period 164 that is sufficient to complete contraction of the agonist muscle. It is also contemplated within the scope of the invention that the first pattern of electrical stimulation pulses may be transmitted at a first intensity level 156 for a period 158 which is sufficient to initiate contraction of the agonist muscle, and at a somewhat lower intermediate intensity level 166 (preferably about 85% of the first intensity level) for a period 168, and at a second intensity level 160 which is less than the first intensity level (preferably about 80% of the first intensity level) for a period 162 that is sufficient to continue contraction of the agonist muscle, and finally at a third intensity level which is greater than the second intensity level (and preferably equal to the first intensity level 156) for a period 164 that is sufficient to complete contraction of the agonist muscle. Preferred first pulse pattern generating circuit 94 is also adapted to generate a first pattern of electrical stimulation pulses having period 162 of the second intensity level that is at least three times greater than period 158 of the first intensity level, and a period 164 of the third intensity level that is not greater than period 158 of the first intensity level.

Preferred second pulse pattern generating circuit 96 is adapted to generate a second pattern of electrical stimulation pulses for transmission through a second pair of electrodes 112 and 113 to the antagonist muscle, at a first intensity level 170 for a period 172 that is sufficient to reduce the acceleration of the limb, and at a second intensity level 174 which is less than the first intensity level (and most preferably 10-30% of the first intensity level) for a period 176 that is sufficient to regulate the movement of the limb, and at a third intensity level which is greater than the second intensity level (and preferably equal to first intensity level 170) for a period 178 that is sufficient to stop the movement of the limb. Preferred second pulse pattern generating circuit 96 is also adapted to generate a second pattern of electrical stimulation pulses having a period 176 of the second intensity level that is 5-15 times greater than period 172 of the first intensity level and not more than five times greater than the period of the third intensity level, and having a period 178 of the third intensity level that is not more than three times greater than period 172 of the first intensity level.

Although this description contains many specifics, these should not be construed as limiting the scope of the invention but as merely providing illustrations of some of the presently preferred embodiments thereof, as well as the best mode contemplated by the inventor of carrying out the invention. The invention, as described herein, is susceptible to various modifications and adaptations, and the same are intended to be comprehended within the meaning and range of equivalents of the appended claims.

What is claimed is:

1. A device for applying neuromuscular electrical stimulation to an agonist/antagonist muscle pair to move a limb about a joint, said device comprising a main stimulator controller and a pulse pattern generating circuitry in communication with the main stimulator controller,
    wherein the main stimulator controller is configured to control said pulse pattern generating circuitry to:
        automatically generate, for each burst period of a plurality of burst periods, a first pattern of electrical stimulation pulses for transmission through a first pair of electrodes to the agonist muscle:
            (i) at a constant first current amplitude level for a period sufficient to initiate contraction of the agonist muscle,
            (ii) at a constant second current amplitude level, less than the first current amplitude level, for a period sufficient to continue contraction of the agonist muscle, the second current amplitude level period consecutive to the first current amplitude level period;
        automatically generate, for each burst period of the plurality of burst periods, a second pattern of electrical stimulation pulses, different from the first pattern, for transmission through the second pair of electrodes to the antagonist muscle:
            (i) at a constant third current amplitude level for a period sufficient to reduce acceleration of the limb,
            (ii) at a constant fourth current amplitude level, less than the third current amplitude level, for a period sufficient to regulate movement of the limb, the fourth amplitude level period consecutive to the third current amplitude level period; and
    wherein each burst period of the plurality of burst periods represents a predetermined period of time during which electrical stimulation is applied to the agonist/antagonist muscle pair.

2. The device of claim 1, wherein each burst period of the plurality of burst periods is followed by a predetermined rest period during which electrical stimulation is not applied to the agonist/antagonist muscle pair.

3. The device of claim 1, wherein each burst period of the plurality of burst periods further includes generating the first pattern of electrical stimulation pulses during a first burst period and generating the second pattern of electrical stimulation pulses during a second burst period that begins after a beginning of the first burst period and ends no later than an end of the first burst period.

4. The device of claim 1, wherein the second current amplitude level is 75-90% of the first current amplitude level, and wherein the fourth current amplitude level is 10-30% of the third current amplitude level.

5. The device of claim 1, wherein the period of the second current amplitude level is at least three times greater than the period of the first current amplitude level, and wherein the period of the fourth current amplitude level is 5-15 times greater than the period of the third current amplitude level.

6. The device of claim 1, wherein the first pattern of electrical stimulation pulses comprises a series of pulses, each of which has a pulse duration that is within a range of 20-400 μsec, and wherein the second pattern of electrical stimulation pulses comprises a series of pulses, each of which has a pulse duration that is within a range of 20-400 μsec.

7. The device of claim 1, wherein the first pattern of electrical stimulation pulses comprises a series of pulses generated at a frequency that is within a range of 20-80 Hz, and wherein the second pattern of electrical stimulation pulses comprises a series of pulses generated at a frequency that is within a range of 20-80 Hz.

8. The device of claim 1, wherein the electrical stimulation pulses in the first pattern of electrical stimulation pulses are generated at current amplitudes within a range of 10-150 mA, and wherein the electrical stimulation pulses in the second pattern of electrical stimulation pulses are generated at current amplitudes within a range of 10-150 mA.

9. The device of claim 1 wherein the first pattern of electrical stimulation pulses comprises a waveform selected from a group consisting of symmetrical biphasic, asymmetrical biphasic, high volt and premodulated, and wherein the second pattern of electrical stimulation pulses comprises a waveform selected from a group consisting of symmetrical biphasic, asymmetrical biphasic, high volt and premodulated.

10. The device of claim 1 wherein each burst period of the plurality of burst periods has a duration between 200 and 5000 msec.

11. The device of claim 1 wherein each burst period is followed by a predetermined rest period during which electrical stimulation is not applied to the agonist/antagonist muscle pair, and each rest period has a duration at least 2-5 times of a duration of the immediately preceding burst period.

12. A system for applying neuromuscular electrical stimulation to an agonist/antagonist muscle pair to move a limb about a joint,
wherein the system includes a main stimulator controller and a stimulation module comprising a pulse pattern generating circuitry in communication with the main stimulator controller,
wherein the stimulation module comprises patterns of electrical stimulation pulses, and wherein the main stimulator controller is configured to control said pulse pattern generating circuitry to:
automatically generate, for each burst period of a plurality of burst periods, a first pattern of electrical stimulation pulses for transmission through a first pair of electrodes to the agonist muscle:
(i) at a constant first current amplitude level for a period sufficient to initiate contraction of the agonist muscle,
(ii) at a constant second current amplitude level, less than the first current amplitude level, for a period sufficient to continue contraction of the agonist muscle, the second current amplitude level period consecutive to the first current amplitude level period,
automatically generate, for each burst period of the plurality of burst periods, a second pattern of electrical stimulation pulses, different from the first pattern, for transmission through the second pair of electrodes to the antagonist muscle:
(i) at a constant third current amplitude level for a period sufficient to reduce acceleration of the limb,
(ii) at a constant fourth current amplitude level, less than the third current amplitude level, for a period sufficient to regulate movement of the limb, the fourth amplitude level period consecutive to the third current amplitude level period; and
wherein each burst period of the plurality of burst periods:
(i) represents a predetermined period of time during which electrical stimulation is applied to the agonist/antagonist muscle pair, and
(ii) is followed by a predetermined rest period during which electrical stimulation is not applied to the agonist/antagonist muscle pair.

13. The system of claim 12, wherein each burst period of the plurality of burst periods further includes generating the first pattern of electrical stimulation pulses during a first burst period and generating the second pattern of electrical stimulation pulses during a second burst period that begins after a beginning of the first burst period and ends no later than an end of the first burst period.

14. The system of claim 12, wherein each rest period has a duration at least 2-5 times of a duration of the immediately preceding burst period.

15. The device of claim 12, wherein the second current amplitude level is 75-90% of the first current amplitude level, and wherein the fourth current amplitude level is 10-30% of the third current amplitude level.

16. The device of claim 12, wherein the period of the second current amplitude level is at least three times greater than the period of the first current amplitude level, and wherein the period of the fourth current amplitude level is 5-15 times greater than the period of the third current amplitude level.

17. The device of claim 12, wherein the first pattern of electrical stimulation pulses comprises a series of pulses, each of which has a pulse duration that is within a range of 20-400 μsec, and wherein the second pattern of electrical stimulation pulses comprises a series of pulses, each of which has a pulse duration that is within a range of 20-400 μsec.

18. The device of claim 12, wherein the first pattern of electrical stimulation pulses comprises a series of pulses generated at a frequency that is within a range of 20-80 Hz, and wherein the second pattern of electrical stimulation pulses comprises a series of pulses generated at a frequency that is within a range of 20-80 Hz.

19. The device of claim 12, wherein the electrical stimulation pulses in the first pattern of electrical stimulation pulses are generated at current amplitudes within a range of 10-150 mA, and wherein the electrical stimulation pulses in the second pattern of electrical stimulation pulses are generated at current amplitudes within a range of 10-150 mA.

20. The device of claim 12 wherein the first pattern of electrical stimulation pulses comprises a waveform selected from a group consisting of symmetrical biphasic, asymmetrical biphasic, high volt and premodulated, and wherein the second pattern of electrical stimulation pulses comprises a waveform selected from a group consisting of symmetrical biphasic, asymmetrical biphasic, high volt and premodulated.

21. The device of claim 12 wherein each burst period of the plurality of burst periods has a duration between 200 and 5000 msec.

* * * * *